United States Patent [19]

Schmitt

[11] Patent Number: 5,912,941
[45] Date of Patent: Jun. 15, 1999

[54] COMMUNICATION SYSTEM FOR USE IN DIAGNOSIS OF AN APPARATUS

[75] Inventor: Thomas Schmitt, Forchheim, Germany

[73] Assignee: Siemens Aktiengesellschaft, Munich, Germany

[21] Appl. No.: 08/928,458

[22] Filed: Sep. 12, 1997

[30] Foreign Application Priority Data

Sep. 12, 1996 [DE] Germany ............................ 196 37 187

[51] Int. Cl.⁶ ................................................... G08C 19/00
[52] U.S. Cl. ........................ 378/91; 378/207; 340/870.28
[58] Field of Search ............................. 378/91, 117, 207,
378/114, 118, 204; 340/635, 653, 679,
825.16, 870.28

[56] References Cited

U.S. PATENT DOCUMENTS

| | | | |
|---|---|---|---|
| 4,158,138 | 6/1979 | Hellstrom | 378/117 X |
| 4,857,918 | 8/1989 | Nukushina et al. | 340/870.01 |
| 4,989,146 | 1/1991 | Imajo | 364/424.04 |
| 4,991,193 | 2/1991 | Cecil et al. | 378/117 |
| 5,422,824 | 6/1995 | Biehler et al. | 364/494 |
| 5,434,900 | 7/1995 | Tanaka et al. | 378/207 X |

FOREIGN PATENT DOCUMENTS 195 05 692A1  8/1996  Germany .

*Primary Examiner*—David P. Porta
*Attorney, Agent, or Firm*—Hill & Simpson

[57] ABSTRACT

Conducting a diagnostic procedure is enabled at the location of an apparatus by providing a transmitter that is fashioned in the form of a hand-held telephone is provided in the apparatus. The transmitter wirelessly communicates with a central station. As a result, the diagnosis system can be remotely activated, and the information thereby obtained can be wirelessly transmitted.

3 Claims, 1 Drawing Sheet

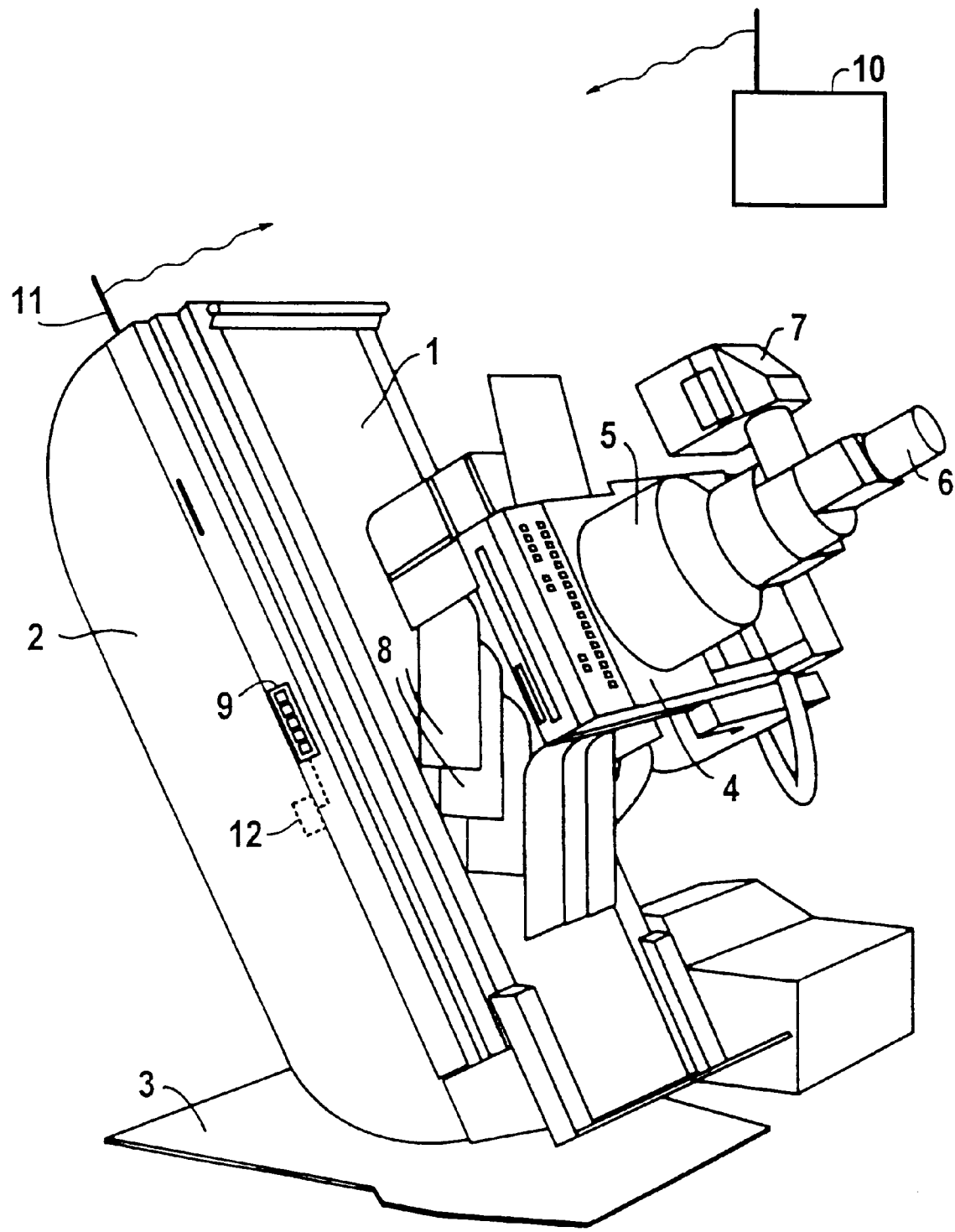

COMMUNICATION SYSTEM FOR USE IN DIAGNOSIS OF AN APPARATUS

BACKGROUND OF THE INVENTION

The present invention generally relates to a communication system. More specifically, the present invention relates to a communication system used with a medical system, such as an X-ray apparatus.

It is known to integrate a diagnostic system in a device that can be activated proceeding from an external diagnostic means via a plug mechanism between the diagnostic means and the device. Such diagnostic systems are employed, for example, in automobiles for motor diagnosis. For the diagnosis, the automobile must be brought into a shop in which a suitable diagnostic means is present for the activation of the diagnostic system. Other devices, for example medical devices, may also potentially require a diagnosis. The error search during diagnosis ensues in a similar way for such devices.

German Patent No. 195 05 692 A1 discloses a printing press to which a video and audio communication system in a control station is allocated. Data exchange for maintenance, diagnosis and repair of the printing press is possible. Also, remote diagnosis and a remote maintenance station are taught. A relatively complicated structure derives in this known system because of the arrangement of the communication system in a control station separated from the printing press.

SUMMARY OF THE INVENTION

The present invention creates a communication system that quickly and reliably enables the diagnosis of a medical apparatus given a simple and compact structure.

In an embodiment, the communication system for the diagnosis of a stand-alone apparatus has a transmitter provided at the apparatus for wireless communication with a central station. The diagnostic system in the apparatus is activated and wirelessly communicates signals corresponding to the result of the diagnosis to the central station.

In an embodiment, the communication system is employed in combination with a medical apparatus. The medical apparatus may be an X-ray apparatus.

The communication system of the present invention has a data transmitter, for example in the form of a handy (hand-held telephone), at the apparatus to be diagnosed. The data transmitter can be activated proceeding from a central station and can then conduct of a diagnostic procedure within the apparatus and transmit corresponding data to the central station. In case of a fault, communication can be set up proceeding from the central station, for example from the factory or from a business location, and a remote diagnosis can be implemented such that, for example, error memories are read out. As a result, designated measures can be initiated by service personnel such as, for example, maintenance and parts replacement. The correct replacement part can be remotely identified and already be brought along to the location of the apparatus for service.

The present invention can be used in medical technology for diagnosis of medical apparatus, for example X-ray equipment.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of an embodiment of the present invention.

DETAILED DESCRIPTION OF THE PRESENTLY PREFERRED EMBODIMENTS

FIG. 1 shows a tiltable X-ray apparatus with a patient bed 1 associated with a frame 2. The frame 2 is tiltably seated on a pedestal 3. Any known means may be implemented by one having ordinary skill in the art to provide a tilting function to the frame 2 and, hence, the bed 1. An X-ray radiator is arranged in the frame 2 in a way that cannot be seen. The image generation ensues with the assistance of an X-ray target 4, an X-ray image intensifier 5 and an image pick-up system following thereupon, namely a video camera 6, and a single frame camera 7. A number of strips 8 of, for example, leaded rubber are provided at the frame of the target 4 for protecting an examining person from laterally emerging radiation from the X-ray apparatus.

A transmitter 9 that belongs to a diagnostic system 12 in the X-ray apparatus is laterally arranged at the X-ray apparatus. The diagnostic system 12 diagnoses the apparatus and supplies corresponding signals as a result of tests generated from testing the apparatus. For example, error memories can be provided for this purpose. The diagnostic system 12 can be wirelessly and/or remotely activated proceeding from a central station 10. To this end, the central station 10 sends corresponding signals that are received by a small antenna 11 at the X-ray apparatus. After the activation, conversely, signals that represent the result of the diagnostic procedure are sent to the central station 10. The signals may be processed, analyzed and/or otherwise displayed at the central station 10. As a result, remote diagnosis is possible in this way.

The invention has been described in conjunction with an X-ray apparatus. However, it is generally suitable for remote diagnosis of any other medical apparatus or arbitrary apparatus.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A communication system for fault diagnosis of an apparatus, comprising:

a stand-alone apparatus which executes an apparatus operation at an apparatus location;

activatable diagnostic means in said stand-alone apparatus for conducting a diagnostic procedure in said stand-alone apparatus to generate a diagnostic result identifying any faults in said apparatus operation;

an apparatus transmitter/receiver in said stand-alone apparatus for wirelessly transmitting said diagnostic result and for wirelessly receiving signals from a location remote from said apparatus location; and a remote transmitter/receiver disposed at said remote location for wirelessly transmitting a signal to said apparatus transmitter/receiver to activate said diagnostic means to conduct said diagnostic procedure, and for wirelessly receiving said diagnostic result transmitted by said apparatus transmitter/receiver.

2. A system as claimed in claim 1 wherein the apparatus comprises a medical apparatus.

3. A system as claimed in claim 2 wherein the medical apparatus comprises an X-ray apparatus.

* * * * *